US010596013B2

(12) United States Patent
Seo

(10) Patent No.: US 10,596,013 B2
(45) Date of Patent: Mar. 24, 2020

(54) WALKING ASSISTANCE APPARATUS AND METHOD OF CONTROLLING THE WALKING ASSISTANCE APPARATUS

(71) Applicant: Samsung Electronics Co., Ltd., Suwon-si, Gyeonggi-do (KR)

(72) Inventor: Keehong Seo, Suwon-si (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 456 days.

(21) Appl. No.: 15/405,457

(22) Filed: Jan. 13, 2017

(65) Prior Publication Data

US 2018/0078390 A1 Mar. 22, 2018

(30) Foreign Application Priority Data

Sep. 20, 2016 (KR) .................. 10-2016-0119984

(51) Int. Cl.
*A61F 2/72* (2006.01)
*A61H 1/02* (2006.01)
*A61H 3/00* (2006.01)
*A61F 2/70* (2006.01)

(52) U.S. Cl.
CPC ............... *A61F 2/72* (2013.01); *A61H 1/024* (2013.01); *A61H 1/0244* (2013.01); *A61H 1/0262* (2013.01); *A61H 1/0266* (2013.01); *A61H 3/00* (2013.01); *A61F 2002/701* (2013.01); *A61H 2201/1215* (2013.01); *A61H 2201/163* (2013.01); *A61H 2201/165* (2013.01); *A61H 2201/1642* (2013.01); *A61H 2201/5069* (2013.01); *A61H 2201/5084* (2013.01)

(58) Field of Classification Search
CPC ........ A61H 3/00; A61H 1/024; A61H 1/0266; A61B 5/11; A61F 2/72
See application file for complete search history.

(56) References Cited

U.S. PATENT DOCUMENTS

2012/0215140 A1 8/2012 Hirata et al.
2013/0226048 A1 8/2013 Unluhisarcikli et al.
(Continued)

FOREIGN PATENT DOCUMENTS

EP 1415770 A1 5/2004
JP 2002301124 A 10/2002
(Continued)

OTHER PUBLICATIONS

Extended European Search Report issued by the European Patent Office dated Aug. 2, 2017 for the corresponding EP Patent Application No. 17152212.1.

*Primary Examiner* — Jason-Dennis N Stewart
(74) *Attorney, Agent, or Firm* — Harness, Dickey & Pierce, P.L.C.

(57) ABSTRACT

A walking assistance apparatus and a method of controlling the walking assistance apparatus are disclosed. The method may include measuring a movement of a hip joint of a user wearing the walking assistance apparatus and a movement of another portion of a body of the user, correcting movement information of the hip joint based on movement information of the other portion of the body, and controlling a torque to be applied to the walking assistance apparatus based on the corrected movement information of the hip joint.

23 Claims, 13 Drawing Sheets

(56) References Cited

U.S. PATENT DOCUMENTS

2013/0237884 A1* 9/2013 Kazerooni ........... A61H 1/0244
601/34
2014/0213951 A1   7/2014 Pietrusisnki et al.
2017/0027801 A1* 2/2017 Choi ................... A61H 1/0244

FOREIGN PATENT DOCUMENTS

| JP | 2010148759 A1 | 7/2010 |
| JP | 2013111378 A | 6/2013 |
| KR | 1020110124924 A | 11/2011 |
| KR | 10-1490885 B1 | 2/2015 |
| KR | 1020150083331 A | 7/2015 |
| KR | 1020150094427 A | 8/2015 |

* cited by examiner

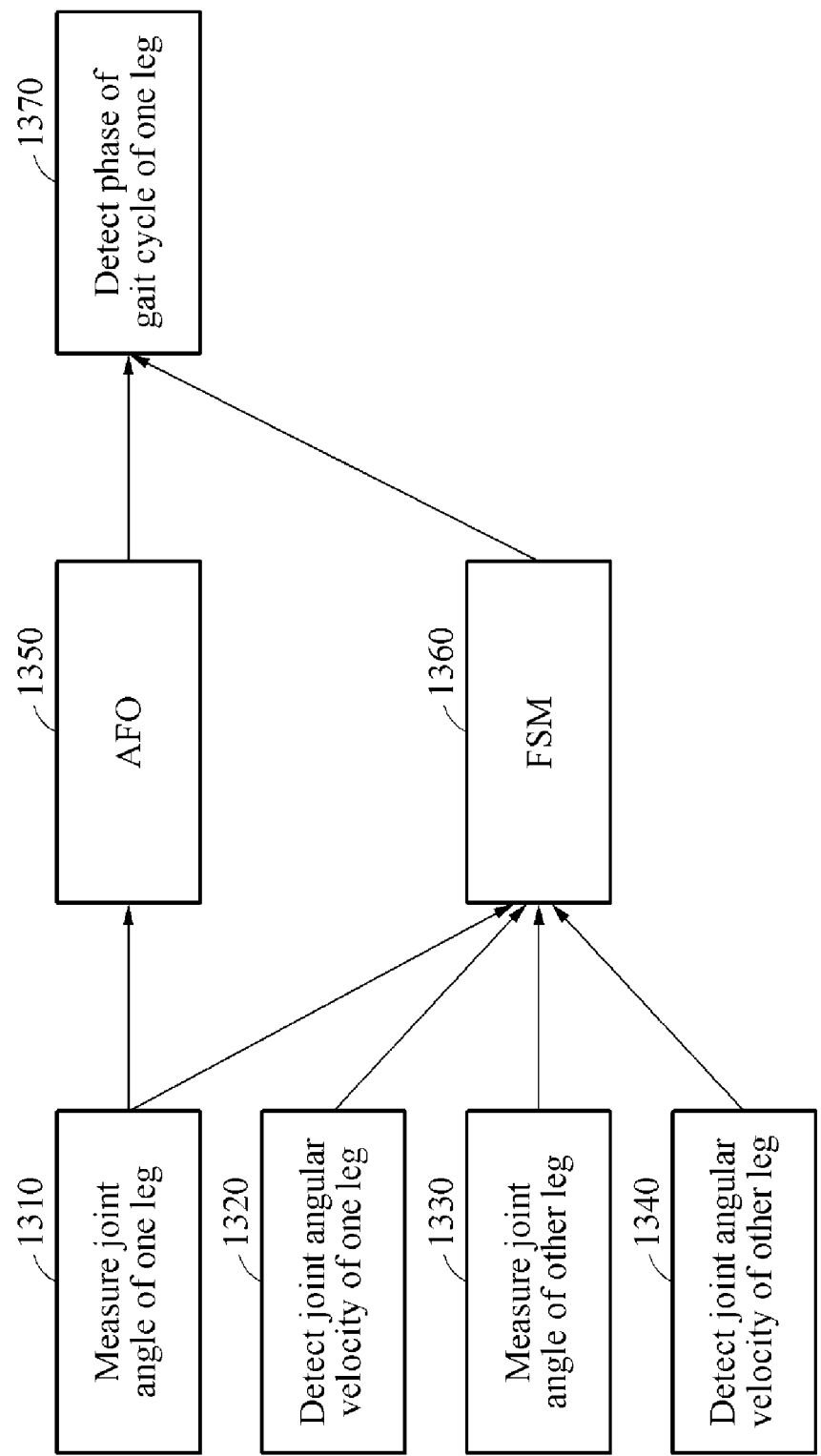

WALKING ASSISTANCE APPARATUS AND METHOD OF CONTROLLING THE WALKING ASSISTANCE APPARATUS

CROSS-REFERENCE TO RELATED APPLICATION

This application claims under 35 U.S.C. § 119 to Korean Patent Application No. 10-2016-0119984 filed on Sep. 20, 2016, in the Korean Intellectual Property Office, the entire contents of which are incorporated herein by reference in their entirety.

BACKGROUND

1. Field

At least one example embodiment relates to a walking assistance apparatus and/or a method of controlling the walking assistance apparatus.

2. Description of the Related Art

A walking assistance apparatus may be used to assist a user who experiences inconvenience in walking with walking more readily. The user may be experiencing such inconveniences for various reasons such as weak leg strength and abnormal joint functions. Such an inconvenience in walking may be attributed to a congenital factor or disease such as a genetic defect, and/or an acquired factor or disease such as an accident and aging of physical functions. A recent issue of aging societies has contributed to diversified uses of a walking assistance apparatus, for example, for assisting an elderly user with weakened muscular strength in walking and increasing muscular strength, in addition to the purposes of a physical therapy and rehabilitation.

SUMMARY

At least one example embodiment relates to a method of controlling a walking assistance apparatus.

In some example embodiments, the method includes measuring a movement of a hip joint of a user associated with the walking assistance apparatus and a movement associated with another portion of a body of the user; correcting movement information of the hip joint based on movement information of the other portion of the body to generate corrected movement information; and controlling a torque to apply to the walking assistance apparatus based on the corrected movement information of the hip joint.

In some example embodiments, the measuring includes measuring a joint angle of the hip joint of the user and a movement of a pelvis of the user, and the correcting includes correcting the measured joint angle of the hip joint based on the movement of the pelvis.

In some example embodiments, the correcting comprises: determining an amount to correct the measured joint angle of the hip joint, if a range of the movement of the hip joint is less than a threshold range.

In some example embodiments, the correcting comprises: correcting the joint angle of the hip joint based on a value obtained by applying a bandpass filter to a rotational angular velocity of the pelvis.

In some example embodiments, the measuring includes measuring a joint angle of the hip joint of the user and an inclination of a trunk of the user, and the correcting includes correcting the joint angle of the hip joint based on the inclination of the trunk.

In some example embodiments, the correcting comprises: determining an amount to correct the joint angle of the hip joint, if the inclination of the trunk is greater than a threshold value.

In some example embodiments, the correcting comprises: subtracting an angle of a forward inclination of the trunk from the joint angle of the hip joint.

In some example embodiments, the measuring includes measuring a joint angle of the hip joint of the user, a movement of a pelvis of the user, and an inclination of a trunk of the user, and the correcting includes correcting the joint angle of the hip joint based on at least one of the inclination of the trunk and the movement of the pelvis.

In some example embodiments, the correcting comprises: correcting the joint angle of the hip joint based on the inclination of the trunk to generate a partially corrected joint angle of the hip joint, if the inclination of the trunk is greater than a threshold value; and correcting the partially corrected joint angle of the hip joint based on the movement of the pelvis, if a range of a movement of the hip joint is less than a threshold range.

In some example embodiments, the controlling comprises: detecting a gait cycle of the user based on the corrected movement information of the hip joint; and determining the torque to apply to the walking assistance apparatus based on the gait cycle.

In some example embodiments, the detecting includes detecting a phase of a gait cycle of a first leg of the user based on the corrected movement information of the hip joint, and the determining includes determining a torque corresponding to the phase of the gait cycle.

In some example embodiments, the measuring comprises: measuring a movement of a hip joint of a first leg of a pair of legs of the user, the first leg being a leg that does not function normally.

Some example embodiments relate to a walking assistance apparatus.

In some example embodiments, the apparatus includes a sensor configured to measure a movement of a hip joint of a user associated with the walking assistance apparatus and a movement of another portion of a body of the user; a driver configured to assist the user in walking; and a processor configured to, correct movement information of the hip joint based on movement information of the other portion of the body to generate corrected movement information, and control a torque to apply to the driver based on the corrected movement information of the hip joint.

In some example embodiments the sensor includes a first sensor configured to measure the movement of the hip joint and a second sensor configured to measure a movement of a pelvis of the user, and the processor is configured to correct a joint angle associated with the movement of the hip joint based on the movement of the pelvis.

In some example embodiments, the sensor includes a first sensor configured to measure the movement of the hip joint and a second sensor configured to measure an inclination of a trunk of the user, and the processor is configured to correct a joint angle associated with the movement of the hip joint based on the inclination of the trunk.

In some example embodiments, the sensor includes a first sensor configured to measure the movement of the hip joint, a second sensor configured to measure a movement of a pelvis of the user, and a third sensor configured to measure an inclination of a trunk of the user, and the processor is configured to correct a joint angle associated with the movement of the hip joint based on the movement of the pelvis and the inclination of the trunk.

In some example embodiments, the first sensor includes at least one of a potentiometer, an absolute encoder, and an incremental encoder, and the second sensor and the third sensor each include at least one of an acceleration sensor, an inclination sensor, an inertial sensor, and a gyrosensor.

Some other example embodiments relate to a method of controlling a walking assistance apparatus.

In some example embodiments, the method includes determining, via a processor, a gait cycle of a user based on a corrected joint angle of a hip joint of the user, the gait cycle of the user being abnormal; and instructing, via the processor, a driver to drive the walking assistance apparatus at a torque level determined based on the gait cycle.

In some example embodiments, the method further includes determining, by the processor, a phase of the gait cycle based on at least one of a particularly-shaped adaptive oscillator (PSAO), an adaptive frequency oscillator (AFO), and a finite state machine (FSM); and determining, by the processor, the torque level from torque data based on the gait cycle, the torque data defining a corresponding relationship between the phase of the gait cycle and the torque level.

In some example embodiments, the method further includes measuring, via one or more sensors, a measured joint angle of the hip joint of the user; measuring, via the one or more sensors, one or more of an inclination of a trunk of the user and a rotational angular velocity of a pelvis of the user; and selectively correcting the measured joint angle based on whether one or more of the inclination of the trunk and the rotational angular velocity of the pelvis is outside a threshold range.

In some example embodiments, the selectively correcting comprises: determining, via the processor, the corrected joint angle based on the measured joint angle of the hip joint and one or more of the inclination of the trunk and the rotational angular velocity of the pelvis.

In some example embodiments, the determining the corrected joint angle comprises: removing, via the processor, an angle of forward inclination of the trunk of the user from the measured joint angle.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 13 is a flowchart illustrating a method of detecting a phase of a gait cycle based on a finite-state machine (FSM) and an adaptive frequency oscillator (AFO) according to at least one example embodiment.

DETAILED DESCRIPTION

Figure 1:
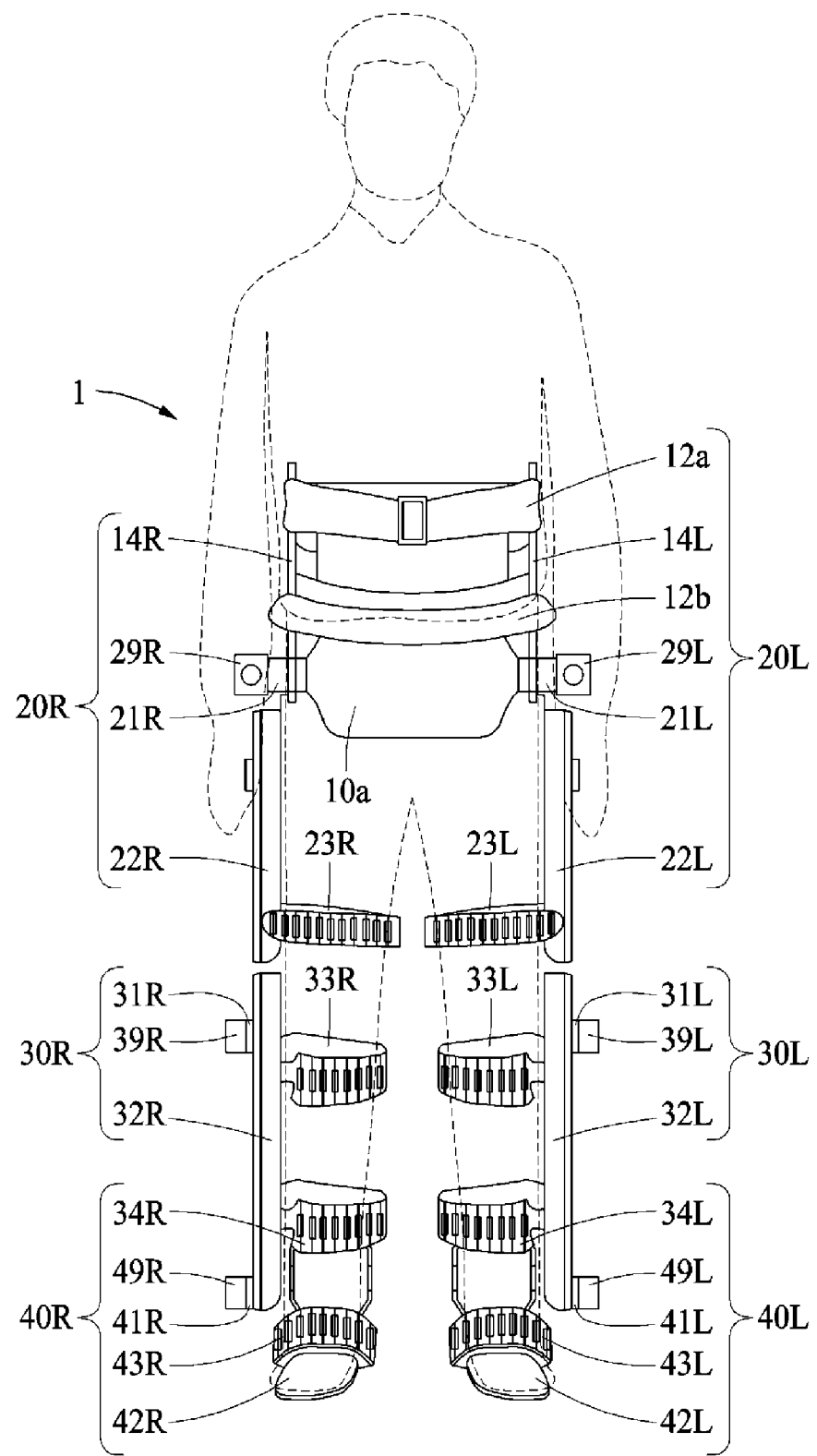
FIG. 1 is a front view illustrating a walking assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Various example embodiments will now be described more fully with reference to the accompanying drawings in which some example embodiments are shown. In the drawings, the thicknesses of layers and regions are exaggerated for clarity.

Figure 2:
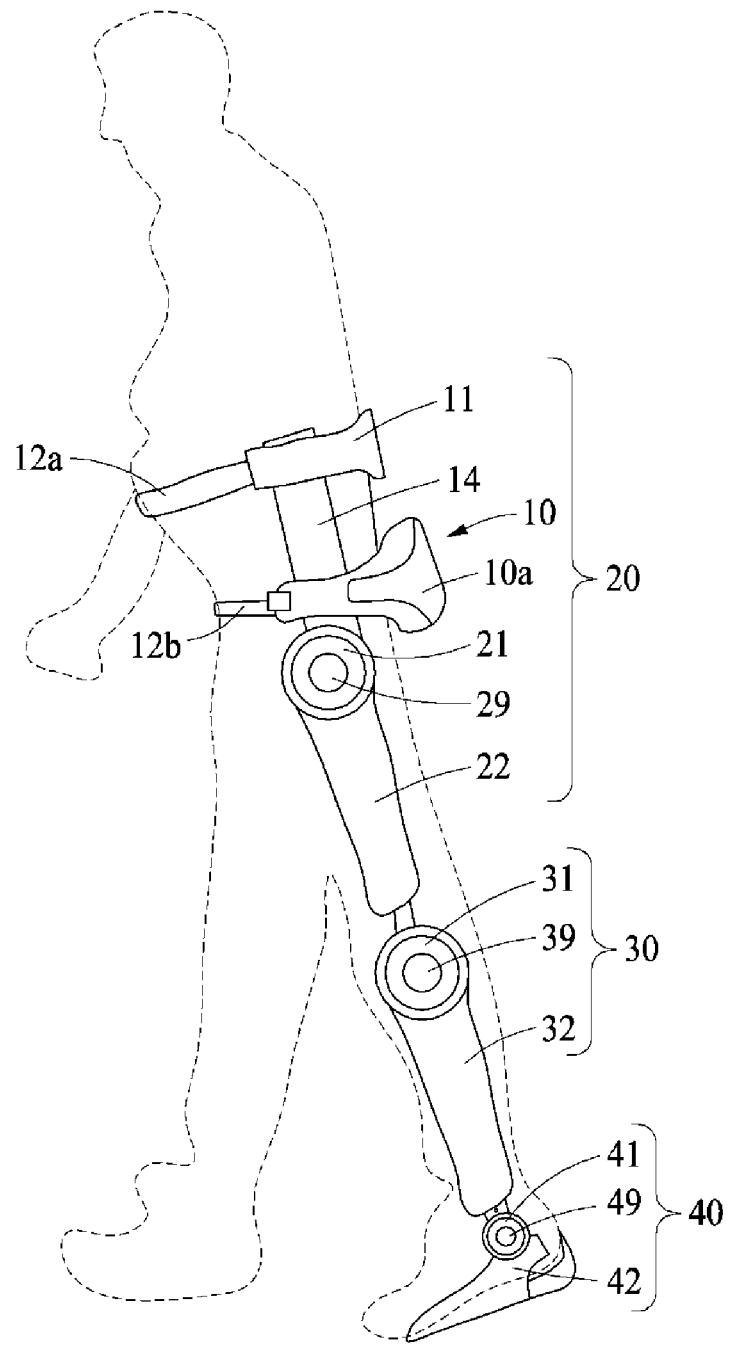
FIG. 2 is a side view illustrating a walking assistance apparatus according to at least one example embodiment.
Figure 3:
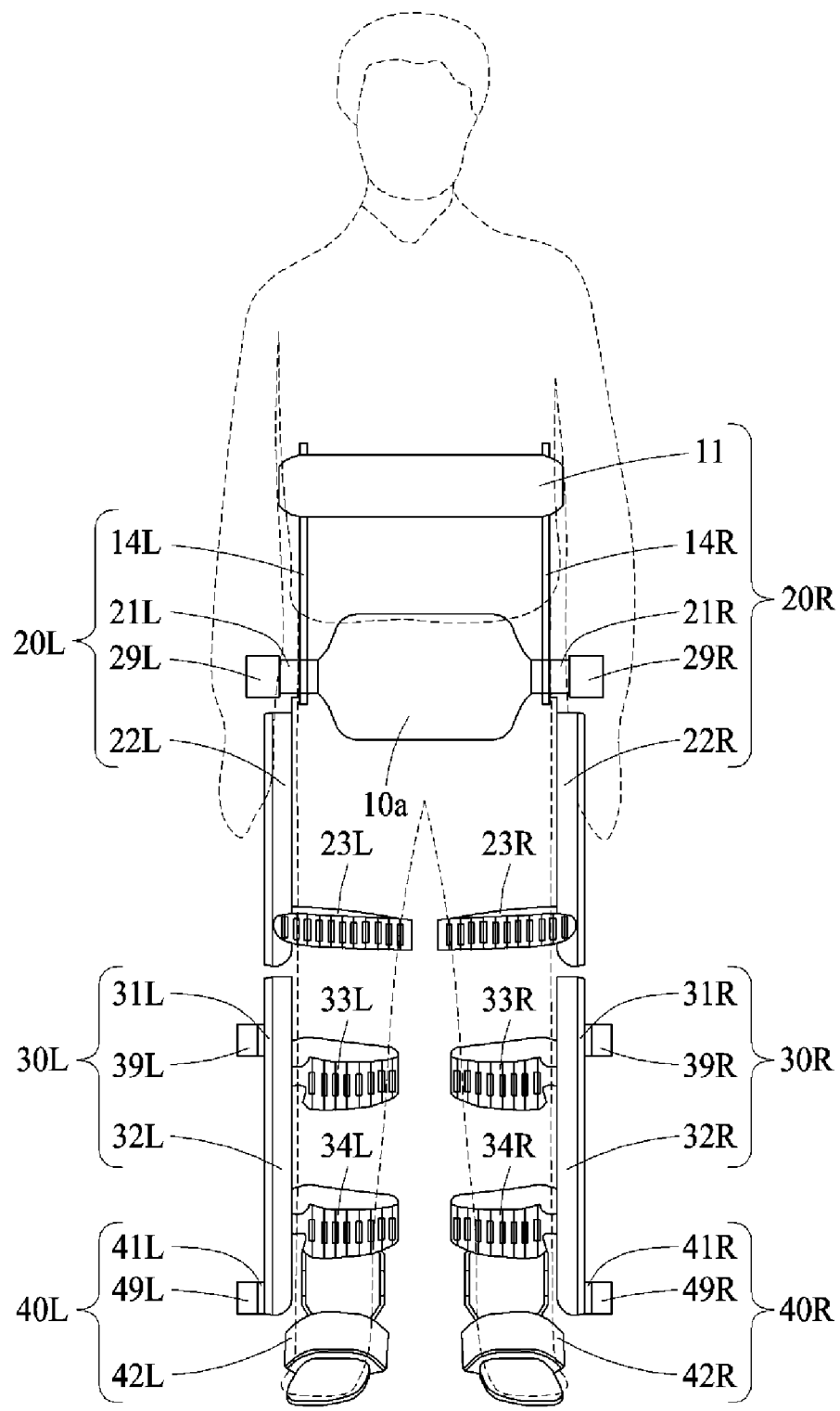
FIG. 3 is a rear view illustrating a walking assistance apparatus according to at least one example embodiment.

FIGS. 1, 2, and 3 are a front view, a side view, and a rear view, respectively, illustrating a walking assistance apparatus 1 according to at least one example embodiment.

The walking assistance apparatus 1 may assist a user wearing the walking assistance apparatus 1 in walking. As illustrated in FIGS. 1 through 3, the walking assistance apparatus 1 may assist both legs of the user, a portion of the legs alternatively, in moving. A type of the walking assistance apparatus 1 illustrated in FIGS. 1 through 3 is provided as an illustrative example only, and thus technical descriptions provided herein may be applicable to any types of the walking assistance apparatus 1.

Referring to FIGS. 1 through 3, the walking assistance apparatus 1 may include a body 10 and walking assistants, for example, a hip joint walking assistant 20, a knee joint walking assistant 30, and an ankle joint walking assistant 40.

The body 10 includes a housing 10a in which various components are embedded. The housing 10a may stably fix the components to the walking assistance apparatus 1 while safely protecting the components in the housing 10a.

The housing 10a includes therein a processor (not shown) configured to process a signal sensed through a sensor and to perform various calculations or computations, or includes various types of a storage device (not shown).

The processor may calculate a gait cycle based on a particularly-shaped adaptive oscillator (PSAO), an adaptive frequency oscillator (AFO), or a finite-state machine (FSM), and determine an assistance torque, or an assistance force, corresponding to the calculated gait cycle. The assistance torque may refer to a rotational force to be applied by the walking assistance apparatus 1 to a body of the user wearing the walking assistance apparatus 1 to assist the user in walking. The processor may generate a control signal to control operations of the walking assistants 20, 30, and 40 based on the determined assistance torque, and transfer the generated control signal to the walking assistants 20, 30, and 40.

The storage device may be, for example, a magnetic disc storage device or a semiconductor memory device, and may store sensing data obtained through the sensor and result data obtained by the processor.

The body 10 further includes a waist support 11 configured to support a waist of the user, a fastener 12a configured to fasten the waist support 11 to the body of the user and/or a fastener 12b configured to fasten the housing 10a to the body of the user. The fasteners 12a and 12b may be, for example, an elastic band or a strap of various types.

Referring to FIGS. 1 through 3, the walking assistance apparatus 1 may include joint movement detectors, for example, a hip joint movement detector 29, a knee joint movement detector 39, and an ankle joint movement detector 49, may measure a movement of a joint, for example, a change in joint angle. A movement of a joint may be represented as a movement of a hinge positioned between different support frames. The joint movement detectors 29, 39, and 49 may be positioned in hinge regions in which the support frames are coupled by hinge mechanism, or positioned respectively in drivers, for example, a hip joint driver 21, a knee joint driver 31, and an ankle joint driver 41, that are configured to provide an assistance torque.

The joint movement detectors 29, 39, and 49 may measure an angle of a joint using an angle sensor, for example, a potentiometer, an absolute encoder, and an incremental encoder. In addition, the joint movement detectors 29, 39, and 49 may include an inertial measurement unit (IMU), for example, a triaxial inertial sensor and a gyrosensor. The IMU may be used to measure an inclination of the body of the user or a walking acceleration and/or speed.

As described above, the walking assistants 20, 30, and 40 includes the hip joint walking assistant 20, the knee joint walking assistant 30, and the ankle joint walking assistant 40. When the user walks, the hip joint walking assistant 20 may assist in a movement of a femoral region and a hip joint of the user, the knee joint walking assistant 30 may assist in a movement of a crural region and a knee joint of the user, and the ankle joint walking assistant 40 may assist in a movement of an ankle joint of the user.

The walking assistance apparatus 1 may include one or two of the hip joint walking assistant 20, the knee joint walking assistant 30, and the ankle joint walking assistant 40, and a gait cycle calculated by any one of the walking assistants 20, 30, and 40 may be used to determine an assistance torque to be output from another walking assistant. The hip joint walking assistant 20, the knee joint walking assistant 30, and the ankle joint walking assistant 40 may be worn on one of a left leg and a right leg of the user, or the both legs of the user.

In a case that the walking assistance apparatus 1 assists both the left leg and the right leg of the user, the hip joint walking assistant 20, the knee joint walking assistant 30, and the ankle joint walking assistant 40 of the walking assistance apparatus 1 may include hip joint walking assistants 20R and 20L, knee joint walking assistants 30R and 30L, and ankle joint walking assistants 40R and 40L, respectively, as illustrated in FIGS. 1 and 3.

The hip joint walking assistants 20R and 20L may provide an assistance torque to the femoral region or the hip joint of the user to assist the user in raising or lowering the femoral region. The hip joint walking assistants 20R and 20L may include the waist fasteners 12a and 12b, thigh fasteners 23R and 23L, hip joint drivers 21R and 21L, first support frames 14R and 14L, second support frames 22R and 22L, and hip joint movement detectors 29R and 29L, respectively.

The waist fasteners 12a and 12b may fasten the first support frames 14R and 14L respectively to the waist of the user, and the thigh fasteners 23R and 23L may fasten the second support frames 22R and 22L respectively to thighs of the user. The hip joint drivers 21R and 21L may generate an assistance torque of various magnitudes in at least one direction, and provide the generated assistance torque to the first support frames 14R and 14L and the second support frames 22R and 22L. Each of the hip joint drivers 21R and 21L may include, for example, a motor configured to generate an assistance torque based on electrical energy supplied by the body 10. The first support frames 14R and 14L and the second support frames 22R and 22L may be physically connected to the hip joint drivers 21R and 21L, and may rotate in at least one direction based on the assistance torque generated by the hip joint drivers 21R and 21L. The hip joint movement detectors 29R and 29L may detect a movement of the hip joint, for example, a joint angle.

The knee joint walking assistants 30R and 30L may provide an assistance torque to the crural region or the knee joint of the user to assist the user in raising or lowering the crural region. The knee joint walking assistants 30R and 30L may include knee fasteners 33R and 33L, shin fasteners 34R and 34L, knee joint drivers 31R and 31L, third support frames 32R and 32L, and knee joint movement detectors 39R and 39L.

The knee fasteners 33R and 33L and the shin fasteners 34R and 34L may fasten the third support frames 32R and 32L to the crural region of the user. The knee joint drivers 31R and 31L may provide an assistance torque of various magnitudes to the third support frames 32R and 32L, and the third support frames 32R and 32L may rotate in at least one direction based on the assistance torque provided by the knee joint drivers 31R and 31L. The knee joint movement detectors 39R and 39L may detect a movement of the knee joint of the user.

The ankle joint walking assistants 40R and 40L may assist in a movement of an ankle of the user when the walking assistance apparatus 1 assists the user in walking. The ankle joint walking assistants 40R and 40L may include the shin fasteners 34R and 34L, foot fasteners 43R and 43L, fourth support frames 42R and 42L, ankle joint drivers 41R and 41L, and ankle joint movement detectors 49R and 49L.

The shin fasteners 34R and 34L and the foot fasteners 43R and 43L may fasten the fourth support frames 42R and 42L to the ankle of the user. Thus, soles of feet of the user may be seated on the fourth support frames 42R and 42L. The ankle joint drivers 41R and 41L may provide an assistance torque of various magnitudes to the fourth support frames 42R and 42L, and the fourth support frames 42R and 42L may rotate in at least one direction based on the assistance torque provided by the ankle joint drivers 41R and 41L. The ankle joint movement detectors 49R and 49L may detect a movement of the ankle joint of the user.

The walking assistance apparatus 1 may assist the user in walking by the components described in the foregoing and operations of the components. The walking assistance apparatus 1 may measure a change in joint angle using the joint movement detectors 29, 39, and 49, estimate a gait cycle, or a phase of the gait cycle, indicating a progression of walking based on the measured change in joint angle, and calculate a torque to be applied to the walking assistants 20, 30, and 40 based on the estimated gait cycle.

A hemiplegic patient with a paralyzed or stiffened leg may tend to walk by rotating a pelvis of the patient to move the paralyzed leg forward. When the patient walking in such a way uses a walking assistance apparatus, there may be no change in joint angle to be measured or there may be only an insignificant change in joint angle.

Figure 4:
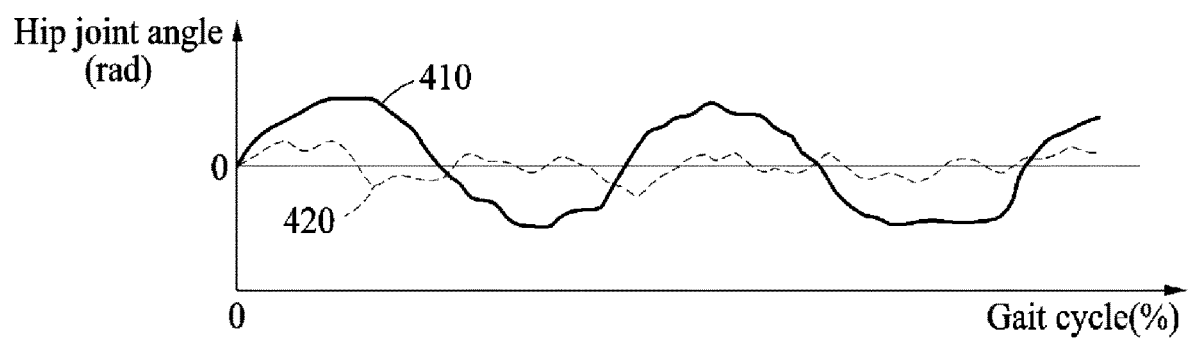
FIGS. 4 and 5 are diagrams illustrating examples of an angle of a hip joint measured from a gait of a hemiplegic patient according to at least one example embodiment.

FIG. 4 is a diagram illustrating an example of an angle of a hip joint measured from a gait of such a hemiplegic patient according to at least one example embodiment.

Referring to FIG. 4, a waveform 410 indicates a change in hip joint angle measured from a normal gait, and a waveform 420 indicates a change in hip joint angle measured from a gait of a paralyzed leg of the hemiplegic patient. In a case of the hemiplegic patient, using the change in hip joint angle measured from the paralyzed leg to estimate a gait cycle or a phase of the gait cycle, may result in misrecognition of the gait cycle and malfunction of the walking assistance apparatus.

Also, a hemiplegic patient may tend to obtain a propulsive force needed for a paralyzed leg of the patient to move by bending and stretching a trunk of the patient.

Figure 5:
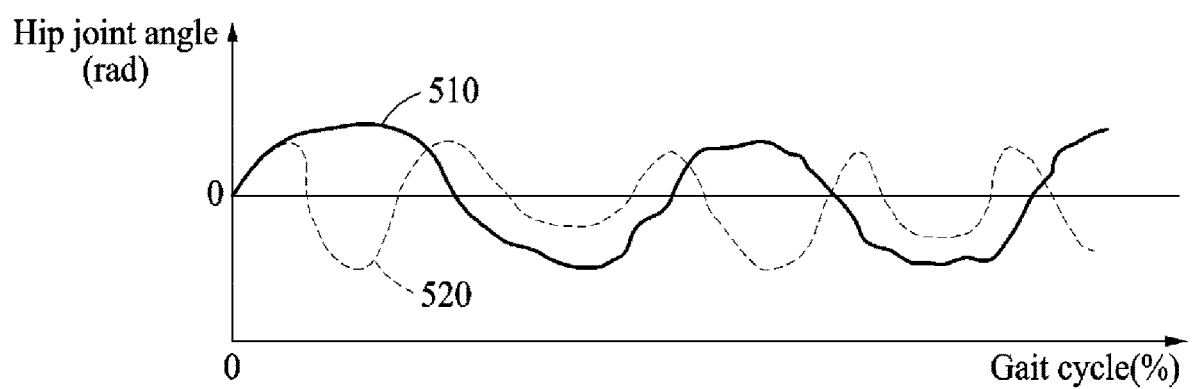

FIG. 5 is a diagram illustrating an example of an angle of a hip joint measured from a gait of such a hemiplegic patient according to at least one example embodiment.

Referring to FIG. 5, a waveform 510 indicates a change in hip joint angle measured from a normal gait, and a waveform 520 indicates a change in hip joint angle measured from a gait of the paralyzed leg of the hemiplegic patient. When the hemiplegic patient bends an upper body or the trunk for the paralyzed leg to move, a result of measuring an angle of a hip joint, or a hip joint angle, of the patient may be represented as an abnormal pattern, and using such result data obtained by the measuring may result in misrecognition of a gait cycle and malfunction of the walking assistance apparatus.

According to at least one example embodiment described herein, a walking assistance apparatus and a method of controlling the walking assistance apparatus may more accurately recognize a gait cycle associated with an abnormal gait pattern such as a pattern shown in a gait of a hemiplegic patient. Hereinafter, operations of the walking assistance apparatus will be described in more detail with reference to FIGS. 6 through 13.

Figure 6:
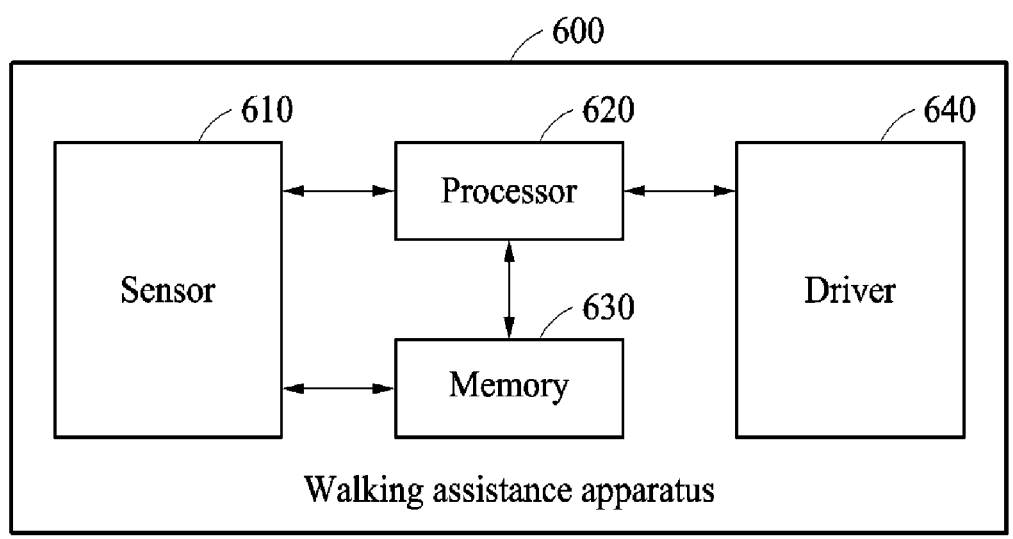
FIG. 6 is a diagram illustrating a configuration of a walking assistance apparatus according to at least one example embodiment.

FIG. 6 is a diagram illustrating a configuration of a walking assistance apparatus 600 according to at least one example embodiment.

The walking assistance apparatus 600 may additionally use movement information of another portion of a body of a user to estimate a gait cycle more accurately. The walking assistance apparatus 600 may correct movement information of a hip joint of the user using the movement information of the other portion of the body, and estimate the gait cycle based on the corrected movement information of the hip joint in order to more accurately recognize a gait cycle of an abnormal gait pattern, such as, for example, a gait pattern of a hemiplegic patient described in the foregoing.

Referring to FIG. 6, the walking assistance apparatus 600 includes a sensor 610, a processor 620, a memory 630, and a driver 640.

The sensor 610 may include sensors configured to measure a movement of a user wearing the walking assistance apparatus 600. For example, the sensor 610 may include a sensor configured to measure a movement of a hip joint of the user, and a sensor configured to measure a movement of another portion of a body of the user excluding the hip joint.

The driver 640 may assist the user in walking by providing an assistance torque to a portion of the body of the user. For example, the driver 640 may include a motor configured to provide a rotational force to a joint of the user.

The processor 620 may include any device capable of processing data including, for example, an application application-specific integrated circuit (ASIC) configured to carry out specific operations based on input data, or a microprocessor configured as a special purpose processor by executing instructions included in computer readable code. The computer readable code may be stored on, for example, a memory (not shown). As discussed in more detail below with reference to FIG. 7, the computer readable code may configure the processor 620 as a special purpose computer to measure, via one or more sensors 610, a measured joint angle of a hip joint of a user, measure, via the one or more sensors 610, one or more of an inclination of a trunk of the user and a rotational angular velocity of a pelvis of the user; selectively correct the measured joint angle based on whether one or more of the inclination of the trunk and the rotational angular velocity of the pelvis is outside a threshold range, determine a gait cycle of a user based on a corrected joint angle of a hip joint of the user, the gait cycle of the user being abnormal; and instruct the driver 640 to drive the walking assistance apparatus 1, 600 at a torque level determined based on the gait cycle.

The processor 620 may generate a control signal to control an operation of the driver 640 based on sensing data obtained from the sensor 610. The processor 620 may correct movement information of the hip joint based on movement information of the other portion of the body of the user, and control a torque to be applied to the driver 640 based on the corrected movement information of the hip joint.

The memory 630 may be a nonvolatile memory device, a volatile memory device, a storage medium, or a combination of two or more of the above-mentioned devices. For example, the memory 630 may include Read Only Memory (ROM), Random Access Memory (RAM), Compact Disk-Read Only Memories (CD-ROMs), magnetic tapes, floppy disks, and an optical recording medium.

The memory 630 may store the sensing data obtained from the sensor 610 and a processing result obtained from calculations or computations performed by the processor 620.

The processor 620 and the driver 640 may correspond to the processor and the drivers 21, 31, and 41, respectively, described with reference to FIGS. 1 through 3. Further, the sensor 610 may correspond to at least the joint movement detector 29. A method of controlling the walking assistance apparatus 600 will be described in detail with reference to FIGS. 7 through 13.

Figure 7:
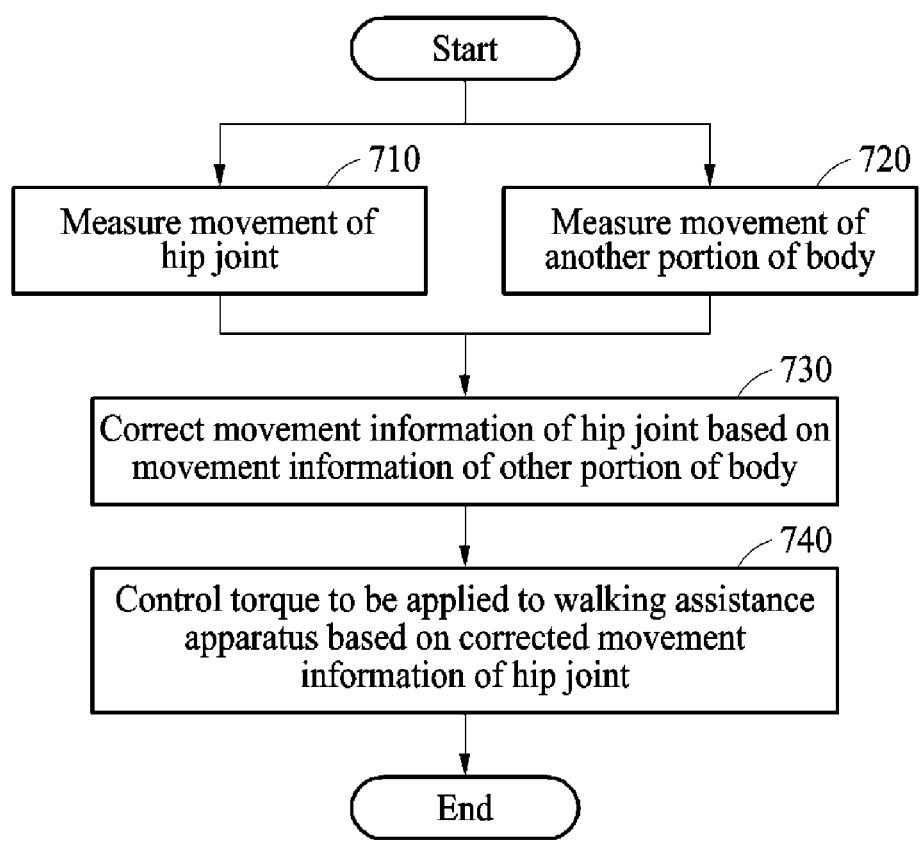
FIG. 7 is a flowchart illustrating a method of controlling a walking assistance apparatus according to at least one example embodiment.

FIG. 7 is a flowchart illustrating a method of controlling the walking assistance apparatus 600 illustrated in FIG. 6.

Referring to FIG. 7, in operation 710, the sensor 610 of the walking assistance apparatus 600 measures a movement of a hip joint of a user wearing the walking assistance apparatus 600. The movement of the hip joint to be measured may be a movement of a hip joint of one leg that does not normally function between two legs of the user, for example, a paralyzed leg of a hemiplegic patient.

In operation 720, the sensor 610 measures a movement of another portion of a body of the user excluding the hip joint, for example, a pelvis and a trunk of the user. In some example embodiments, the processor 620 may instruct the sensor 610 to perform operations 710 and 720 simultaneously. In other example embodiments, operations 710 and 720 may be performed sequentially in various orders.

In operation 730, the processor 620 of the walking assistance apparatus 600 corrects movement information of the hip joint based on movement information of the other portion of the body of the user. Examples of a method of correcting the movement information of the hip joint by the processor 620 based on the movement information of the other portion of the body of the user will be described in more detail with reference to FIGS. 8 through 10.

In operation 740, the processor 620 controls a torque applied to the walking assistance apparatus 600 based on the corrected movement information of the hip joint. A method of controlling the torque to be applied to the walking assistance apparatus 600 by the processor 620 will be described in more detail with reference to FIG. 11.

Figure 8:
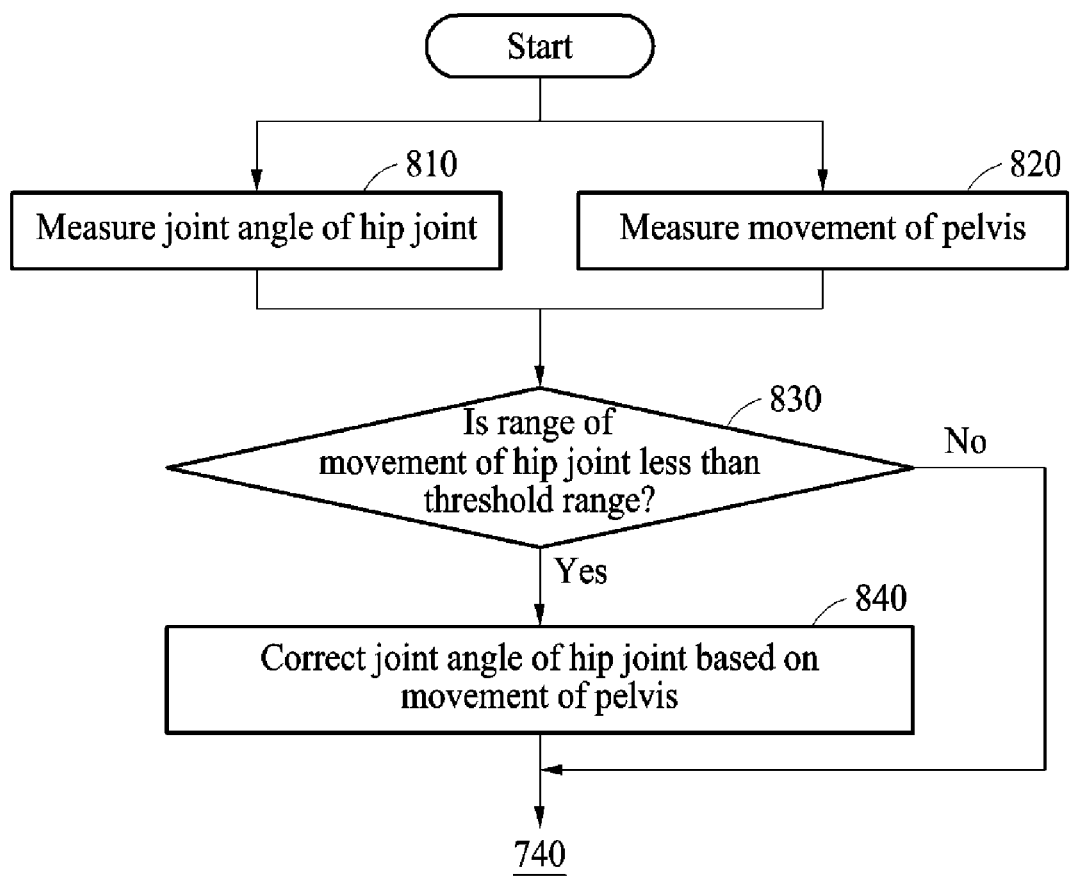
FIGS. 8 through 10 are flowcharts illustrating examples of a method of correcting movement information of a hip joint according to at least one example embodiment.

An Example of a Method of Correcting Movement Information of a Hip Joint According to at Least One Example Embodiment FIG. 8 is a flowchart illustrating an example of a method of correcting movement information of a hip joint according to at least one example embodiment. When a user wearing a walking assistance apparatus rotates a pelvis of the user to move one leg forward, for example, when a hemiplegic patient rotates a pelvis of the patient to move a paralyzed leg of the patient forward, the wearing assistance apparatus may correct movement information of a hip joint based on a movement of the pelvis, and thus more accurately recognize a gait cycle based on the corrected movement information of the hip joint.

Referring to FIG. 8, in operation 810, a first sensor included in the sensor 610 of the walking assistance apparatus 600 illustrated in FIG. 6 measures a joint angle of a hip joint of a user wearing the walking assistance apparatus 600. The first sensor may include, for example, a potentiometer, an absolute encoder, or an incremental encoder, to sense a joint angle.

In operation 820, a second sensor included in the sensor 610 measures a movement of a pelvis of the user as a movement of a trunk of the user. The second sensor may include at least one of, for example, an acceleration sensor, an inertial sensor, and a gyrosensor, and be disposed in the vicinity of the pelvis of the user. In some example embodiments, the processor 620 may instruct the sensor 610 to perform operations 810 and 820 simultaneously. In other example embodiments, operations 910 and 920 may be performed sequentially in various orders.

The processor 620 of the walking assistance apparatus 600 may obtain information associated with a rotation angle of the pelvis by applying a bandpass filter to sensing information obtained from the second sensor.

In operation 830, the processor 620 determines whether a range of a movement, for example, a range of motion (ROM), of the hip joint that is associated with the measured joint angle of the hip joint is less than a threshold range.

In operation 840, when the range of the movement of the hip joint is less than the threshold range, the processor 620 corrects the joint angle of the hip joint measured in operation 810 based on the measured movement of the pelvis. For example, the processor 620 may correct the joint angle of the hip joint based on the movement of the pelvis as represented by Equation 1 below.

$$\theta_2 = sr\omega + \theta_1 \qquad \text{[Equation 1]}$$

In Equation 1, $\theta_1$ and $\theta_2$ denote a measured joint angle of a hip joint and a corrected joint angle of the hip joint, respectively. Regarding a sign of $\theta_1$, $\theta_1$ has a positive value when a leg moves forward from a trunk, and has a negative value when the leg moves backward from the trunk. $\omega$ denotes a value obtained by applying a bandpass filter to a rotational angular velocity of a pelvis. The rotational angular velocity of the pelvis may reflect a rotational velocity of the pelvis relative to an axis in a vertical direction, and may be obtained based on sensing data obtained through the second sensor. r denotes an adjustable constant. s denotes a constant, which may be −1 in a case of a hip joint of a left leg and +1 in a case of a hip joint of a right leg.

When a user rotates a pelvis of the user to walk, a change in the joint angle $\theta_2$ corrected based on Equation 1 may be more salient compared to a change in the measured joint angle $\theta_1$, and thus a gait cycle of the user may be recognized more accurately. For example, through a correction, measurement data as shown in the waveform 420 illustrated in FIG. 4 may change to be similar to the waveform 410 illustrated in FIG. 4.

When the range of the movement of the hip joint is not less than the threshold range, the processor 620 may not correct the joint angle of the hip joint, and instead may control a torque to be applied to the walking assistance apparatus 600 based on the joint angle of the hip joint measured in operation 810, as described in operation 740 of FIG. 7.

Figure 9:
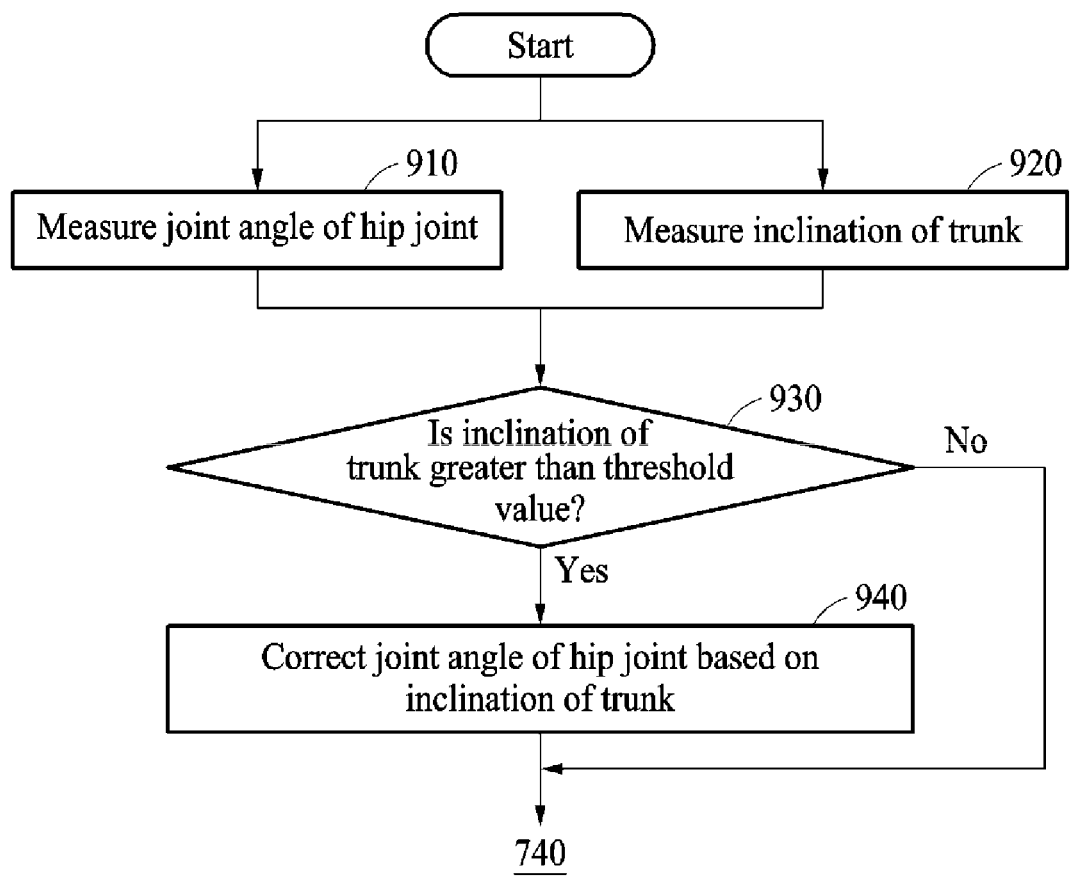

Another Example of a Method of Correcting Movement Information of a Hip Joint According to at Least One Example Embodiment FIG. 9 is a flowchart illustrating another example of a method of correcting movement information of a hip joint according to at least one example embodiment.

When a user wearing a walking assistance apparatus bends and stretches an upper body or a trunk of the user to move one leg forward, for example, when a hemiplegic patient bends and stretches an upper body of the patient to obtain a propulsive force for a paralyzed leg of the patient to move, the wearing assistance apparatus may correct movement information of a hip joint of the user based on an inclination of the trunk of the user, and thus more accurately recognize a gait cycle based on the corrected movement information of the hip joint.

Referring to FIG. 9, in operation 910, the first sensor included in the sensor 610 of the walking assistance apparatus 600 illustrated in FIG. 6 measures a joint angle of a hip joint of a user wearing the walking assistance apparatus 600, as described in operation 810 of FIG. 8.

In operation 920, a third sensor included in the sensor 610 measures an inclination of a trunk of the user in a gravitational direction. The third sensor may include at least one of, for example, an acceleration sensor, an inclination sensor, an inertial sensor, and a gyrosensor, and be positioned on a waist or a back of the user. In some example embodiments, the processor 620 may instruct the sensor 610 to perform operations 910 and 920 simultaneously. In other example embodiments, operations 910 and 920 may be performed sequentially in various orders.

In operation 930, the processor 620 of the walking assistance apparatus 600 determines whether the measured inclination of the trunk is greater than a threshold value.

In operation 940, when the measured inclination of the trunk is greater than the threshold value, the processor 620 corrects the joint angle of the hip joint measured in operation 910 based on the measured inclination of the trunk. For example, the processor 620 may correct the joint angle of the hip joint based on the inclination of the trunk as represented by Equation 2 below.

$$\theta_2 = \theta_1 - \psi \qquad \text{[Equation 2]}$$

In Equation 2, $\theta_1$ and $\theta_2$ denote a measured joint angle of a hip joint of a user and a corrected joint angle of the hip joint, respectively. Regarding a sign of $\theta_1$, $\theta_1$ has a positive value when a leg moves forward from a trunk, and a negative value when the leg moves backward from the trunk. $\psi$ denotes an angle of a forward inclination of a trunk or an upper body of the user, and has a positive value when the trunk is inclined forwards from a vertical direction in which the user stands, and a negative value when the trunk is inclined backwards. Based on Equation 2, by subtracting the angle $\psi$ of the forward inclination of the trunk from the measured joint angle $\theta_1$ of the hip joint, an element associated with the inclination of the trunk may be eliminated.

Although the measured joint angle $\theta_1$ may be indicated by an abnormal change pattern when the user bends and stretches the trunk to walk, the abnormal change pattern of the joint angle of the hip joint may be improved to be a normal pattern by correcting the joint angle $\theta_1$ based on Equation 2. For example, through a correction, the abnormal change pattern such as shown in the waveform 520 illustrated in FIG. 5 may change to be similar to the waveform 510 illustrated in FIG. 5.

When the measured inclination of the trunk is not greater than the threshold value, the processor 620 may not correct the joint angle of the hip joint, and instead may control a torque to be applied to the walking assistance apparatus 600 based on the joint angle of the hip joint measured in operation 910, as described in operation 740 of FIG. 7.

Figure 10:
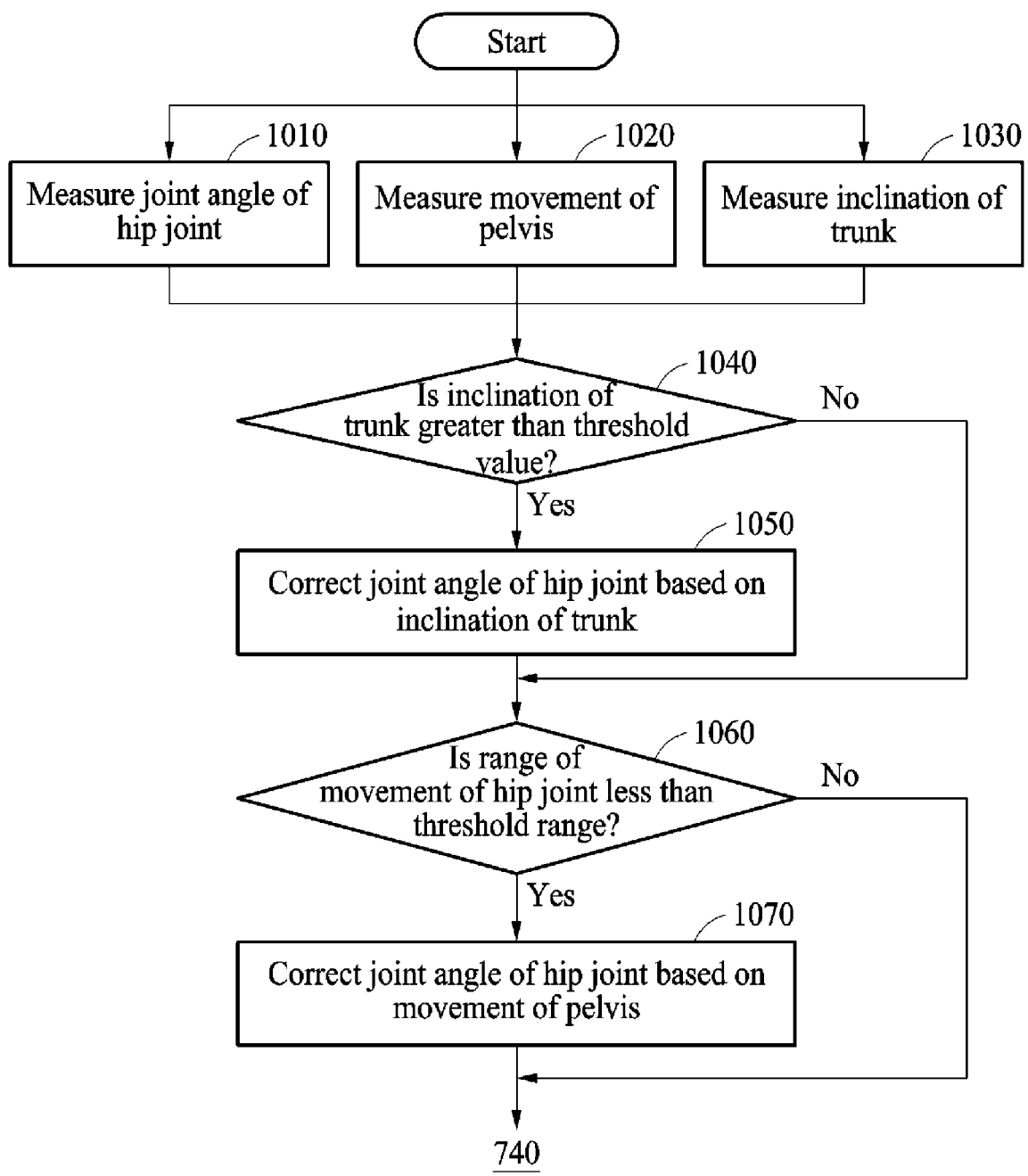

Still Another Example of a Method of Correcting Movement Information of a Hip Joint According to at Least One Example Embodiment FIG. 10 is a flowchart illustrating still another example of a method of correcting movement information of a hip joint according to at least one example embodiment. A walking assistance apparatus may correct movement information of a hip joint based on one of a movement of a pelvis and an inclination of a trunk as described with reference to FIGS. 8 and 9, and may also determine whether to correct the joint angle of the hip joint based on both the movement of the pelvis and the inclination of the trunk as described hereinafter with reference to FIG. 10.

Referring to FIG. 10, in operation 1010, a first sensor included in the sensor 610 of the walking assistance apparatus 600 illustrated in FIG. 6 may measure a joint angle of a hip joint of a user.

In operation 1020, a second sensor included in the sensor 610 measures a movement of a pelvis of the user.

In operation 1030, a third sensor included in the sensor 610 measures an inclination of a trunk of the user.

For descriptions of operations 1010 through 1030, reference may be made to the descriptions of operations 810 and 820 of FIG. 8, and operations 910 and 920 of FIG. 9. In some example embodiments, the processor 620 may instruct the sensor 610 to perform operations 1010, 1020 and 1030 simultaneously. In other example embodiments, operations 1010, 1020 and 1030 may be performed sequentially in various orders.

In operation 1040, the processor 620 of the walking assistance apparatus 600 may determine whether the measured inclination of the trunk is greater than a threshold value.

In operation 1050, when the measured inclination of the trunk is greater than the threshold value, the processor 620 corrects the joint angle of the hip joint measured in operation 1010. For example, the processor 620 may perform correction in operation 1050 based on Equation 2.

In operation 1060, the processor 620 may determine whether a range of a movement associated with the joint angle of the hip joint corrected in operation 1050 is less than a threshold range.

In operation 1070, when the range of the movement range associated with the corrected joint angle is less than the threshold range, the processor 620 may additionally correct the corrected joint angle of the hip joint based on the measured movement of the pelvis. As described above, the processor 620 may correct the joint angle of the hip joint based on both the inclination of the trunk and the movement of the pelvis using Equation 3 below.

$$\theta_2 = \theta_1 - \psi + sr\omega \qquad \text{[Equation 3]}$$

In Equation 3, $\theta_1$ and $\theta_2$ denote a measured joint angle of a hip joint of a user and a corrected joint angle of the hip joint, respectively. $\omega$ denotes a value obtained by applying a bandpass filter to a rotational angular velocity of a pelvis of the user, and corresponds to $\omega$ in Equation 1. $\psi$ denotes an angle of a forward inclination of a trunk or an upper body of the user, and corresponds to ψ in Equation 2.

Referring back to operation 1040, when the measured inclination of the trunk is not greater than the threshold value, the processor 620 may not correct the joint angle of the hip joint based on the inclination of the trunk, and skips to operation 1060.

In operation 1060, the processor 620 may determine whether a range of a movement of the hip joint associated with the joint angle of the hip joint measured in operation 1010 is less than a threshold range. In operation 1070, when the range of the movement associated with the measured joint angle of the hip joint is less than the threshold range, the processor 620 corrects the joint angle of the hip joint based on the movement of the pelvis. As described herein, the processor 620 may correct the joint angle of the hip joint based on Equation 1.

While FIG. 10 illustrates an example embodiment in which the processor 620 first analyses the trunk information in operations 1040 and 1050 prior to analyzing the movement information in operations 1060 and 1070, example embodiments are not limited thereto. For example, in other example embodiments the processor 610 may perform operations 1060 and 1070 prior to performing operations 1040 and 1050.

Although not shown, in other example embodiments, the processor 620 may act as a safety mechanism and disable providing the assistance torque to the user based on an amount of the inclination and the range of movement of the hip joint.

For example, if the processor 620 determines in operations 830 or 1060, that the range of movement of the hip joint of the user is less than a minimum range of movement and/or determines, in operations 930 or 1040, that the inclination of the trunk is greater than a maximum inclination, the processor 620 may instruct the drivers 21, 31, 41 to turn off rather than correcting the joint angle of the hip joint and using the corrected joint angle to determine an assistance torque provided by one or more of the drivers 21, 31, 41. Therefore, the processor 620 may operate as a safety mechanism to prevent a user with a full paralysis of one side of their body from sustaining further injury.

Figure 11:
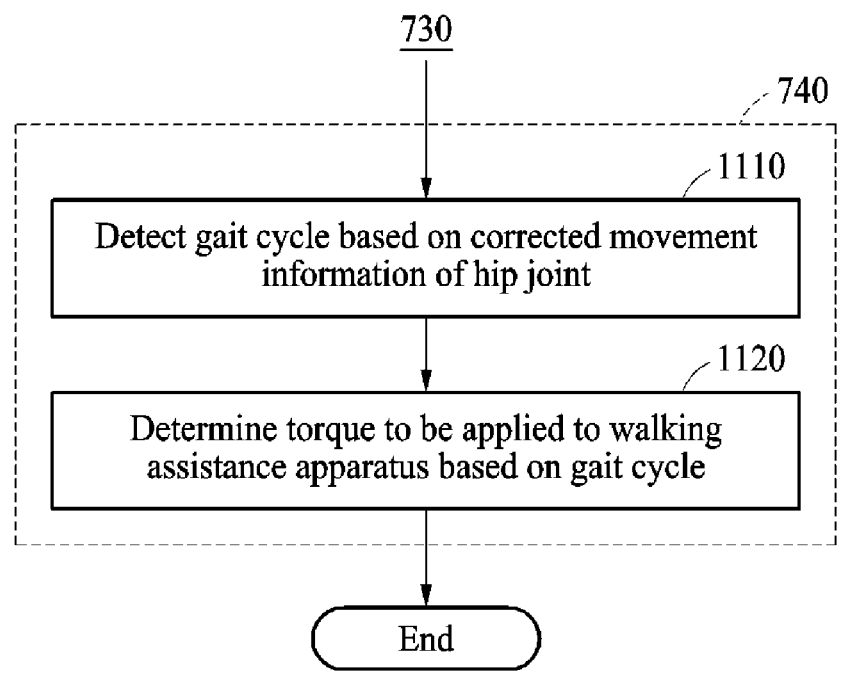
FIG. 11 is a flowchart illustrating a method of controlling a torque to be applied to a walking assistance apparatus according to at least one example embodiment.

FIG. 11 is a flowchart illustrating a method of controlling a torque to be applied to a walking assistance apparatus according to at least one example embodiment.

Referring to FIG. 11, in operation 1110, the processor 620 of the walking assistance apparatus 600 illustrated in FIG. 11 detects a gait cycle of a user based on corrected movement information of a hip joint of the user.

The processor 620 may detect a phase of the gait cycle using at least one of a PSAO, an AFO, or an FSM.

An example of the processor 620 detecting the phase of the gait cycle using the PSAO is discussed in more detail below with reference to FIG. 12. Further, an example of the processor 620 detecting the phase of the gait cycle based on the FSM and the AFO is discussed in more detail below with reference to FIG. 13.

For example, the processor 620 may determine a gait state through the FSM, and determine the phase of the gait cycle based on the determined gait state. A requirement for transition among gait states included in the FSM may be set using an angle and an angular velocity of each of a right hip joint and a left hip joint at a point at which respective angles and respective angular velocities of the right hip joint and the left hip joint cross. For example, the gait states included in the FSM may include a state in which a left leg swings while being supported by a right leg, a state in which the left leg swung while being supported by the right leg lands on the ground, a state in which the right leg swings while being supported by the left leg, and a state in which the right leg swung while being supported by the left leg lands on the ground.

The gait cycle refers to one cycle or period starting from a point in time at which one foot touches the ground, and lasting until the foot touches the ground again, and may be defined as a variable that increases linearly during one cycle. For example, in the gait cycle, a point in time at which one foot touches the ground may be defined as 0%, which increases linearly during one gait cycle, and then a point in time immediately before the foot touches the ground again may be defined as 100%.

In operation 1120, the processor 620 determines a torque to be applied to the walking assistance apparatus 600 based on the detected gait cycle. The processor 620 may determine a torque corresponding to the phase of the gait cycle determined in operation 1110 to be applied to the driver 640 of the walking assistance apparatus 600. In some example embodiments, the processor 620 may determine the torque corresponding to the phase of the gait cycle using a lookup table. In some example embodiments, the lookup table may be predefined, however, example embodiments are not limited thereto. The lookup table may include a data set defining a corresponding relationship between the phase of the gait cycle and the torque. Also, the lookup table may include a plurality of data sets that are classified based on a slope of the ground, a walking speed of the user, an age of the user, a gender of the user, or a weight of the user. An assistance torque that may assist the user in walking may be obtained based on the torque applied to the driver 640.

Figure 12:
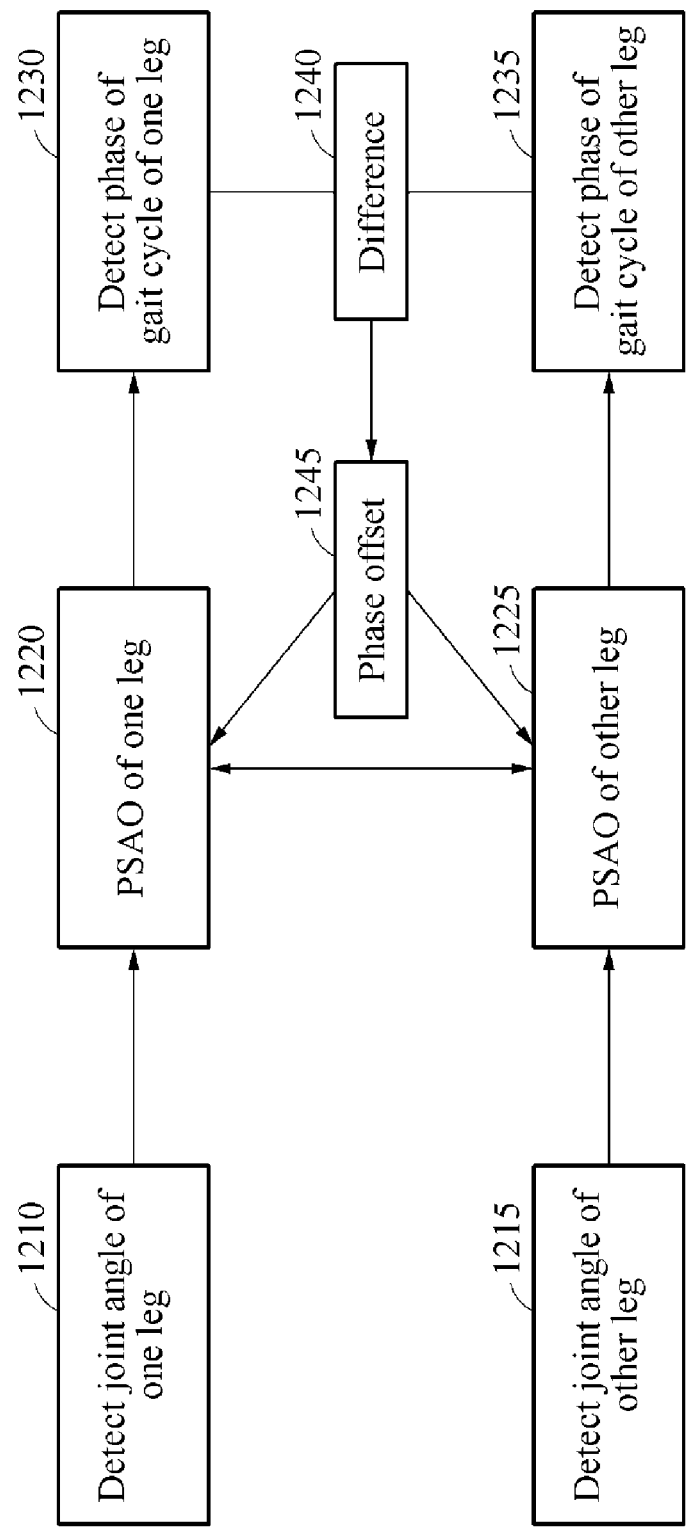
FIG. 12 is a diagram illustrating a method of detecting a phase of a gait cycle based on a particularly-shaped adaptive oscillator (PSAO) according to at least one example embodiment.

FIG. 12 is a diagram illustrating a method of detecting a phase of a gait cycle based on a PSAO according to at least one example embodiment.

Referring to FIG. 12, in operation 1210, the processor 620 of the walking assistance apparatus 600 illustrated in FIG. 6 may detect a joint angle of a first leg, for example of, a joint angle of a first hip joint associated with the first leg.

In operation 1215, the processor 620 detects a joint angle of a second leg, for example, a joint angle of a second hip joint associated with the second leg.

In operation 1220, the processor 620 calculates a gait frequency of the first leg using a PSAO. The PSAO may include a plurality of oscillators having an offset, a fundamental frequency, or a frequency obtained by modulating the fundamental frequency. The frequency obtained by modulating the fundamental frequency may be an integer multiple frequency of the fundamental frequency. Each of the oscillators may have a phase and amplitude.

The PSAO may obtain an angle of each of the oscillators by applying a reference trajectory, a phase, and amplitude to each of the oscillators having the fundamental frequency and a frequency corresponding to an integer multiple of the fundamental frequency. The PSAO may generate an overlapping angle by overlapping the respective angles obtained from the oscillators. The PSAO may generate an overlapping angle trajectory by combining the generated overlapping angles in order of the gait cycle. The PSAO may then repetitively correct the fundamental frequency, the offset, and the phases and amplitudes of the oscillators to minimize an error between the overlapping angle and the measured joint angle.

Through such a correction, the overlapping angle trajectory may be approximated to a trajectory of the measured joint angle. The fundamental frequency, the offset, and the amplitudes of the oscillators may converge on a value to correspond to the trajectory of the measured joint angle. When the generated overlapping angle trajectory corresponds to the trajectory of the measured joint angle, the fundamental frequency of the PSAO may correspond to the gait frequency. A phase of an oscillator having the fundamental frequency may correspond to a current gait phase, and the gait cycle may be detected based on the gait phase.

In operation 1230, the processor 620 detects a phase of a gait cycle of the first leg using the gait frequency. For example, the processor 620 may detect the phase of the gait cycle using a phase-compensated adaptive oscillator (PCAO). The PCAO may be, for example, a signal processing module that uses the measured joint angle of the hip joint as an input, and outputs a current phase of the gait cycle. The detected phase of the gait cycle of the first leg is referred to as a first phase.

In operation 1225, similarly to operation 1220, the processor 620 calculates a gait frequency of the second leg using a PSAO of the second leg. In operation 1235, similarly to operation 1230, the processor 620 detects a phase of a gait cycle of the other leg using the gait frequency. The detected phase of the gait cycle of the second leg is referred to as a second phase.

In operation 1240, the processor 620 calculates a difference between the first phase and the second phase. For example, the difference between the first phase and the second phase may be 50% in a case of a normal gait. For another example, the difference between the first phase and the second phase may not be 50% in a case of an abnormal gait.

In operation 1245, the processor 620 sets a phase offset in the PSAO of the first leg and in the PSAO of the second leg. For the normal gait, the phase offset may be set to be 180 degrees (°), for example, a gait cycle being 50%. For the abnormal gait, a phase offset at which an asymmetrical gait cycle is recognized may be set.

FIG. 13 is a flowchart illustrating a method of detecting a phase of a gait cycle based on an FSM and an AFO according to at least one example embodiment.

Referring to FIG. 13, in operation 1310, the processor 620 of the walking assistance apparatus 600 illustrated in FIG. 6 measures a joint angle of a first leg, for example, a joint angle of a first hip joint associated with the first leg.

In operation 1320, the processor 620 detects a joint angular velocity of the leg.

In operation 1330, the processor 620 measures a joint angle of a second leg, for example, a joint angle of a second hip joint associated with the second leg.

In operation 1340, the processor 620 detects a joint angular velocity of the second leg.

In operation 1350, the processor 620 calculates a current gait frequency based on an AFO. For example, the processor 620 may calculate the current gait frequency based on the joint angle of the first leg.

In operation 1360, the processor 620 determines a current gait state among preset gait states using an FSM. For example, the processor 620 may determine the current gait state based on the joint angle and the joint angular velocity of the first leg, and the joint angle and the joint angular velocity of the second leg.

In operation 1370, the processor 620 detects a phase of a gait cycle of the first leg based on at least one of the calculated current gait frequency and the determined current gait state.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments.

For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of controlling a walking assistance apparatus, the method comprising:
    measuring, using a sensor of the walking assistance apparatus, a movement of a hip joint of a user associated with the walking assistance apparatus and a movement associated with another portion of a body of the user;
    correcting movement information of the hip joint based on movement information of the other portion of the body to generate corrected movement information; and
    controlling a torque to apply to a driver of the walking assistance apparatus based on the corrected movement information of the hip joint, wherein
    the driver is configured to assist the user in walking.

2. The method of claim 1, wherein
    the measuring includes measuring a joint angle of the hip joint of the user and a movement of a pelvis of the user, and
    the correcting includes correcting the joint angle of the hip joint based on the movement of the pelvis.

3. The method of claim 2, wherein the correcting comprises:
    determining an amount to correct the measured joint angle of the hip joint, if a range of the movement of the hip joint is less than a threshold range.

4. The method of claim 2, wherein the correcting comprises:
    correcting the joint angle of the hip joint based on a value obtained by applying a bandpass filter to a rotational angular velocity of the pelvis.

5. The method claim 1, wherein
    the measuring includes measuring a joint angle of the hip joint of the user and an inclination of a trunk of the user, and
    the correcting includes correcting the joint angle of the hip joint based on the inclination of the trunk.

6. The method of claim 5, wherein the correcting comprises:
    determining an amount to correct the joint angle of the hip joint, if the inclination of the trunk is greater than a threshold value.

7. The method of claim 5, wherein the correcting comprises:
    subtracting an angle of a forward inclination of the trunk from the joint angle of the hip joint.

8. The method of claim 1, wherein
    the measuring includes measuring a joint angle of the hip joint of the user, a movement of a pelvis of the user, and an inclination of a trunk of the user, and
    the correcting includes correcting the joint angle of the hip joint based on at least one of the inclination of the trunk and the movement of the pelvis.

9. The method of claim 8, wherein the correcting comprises:
    correcting the joint angle of the hip joint based on the inclination of the trunk to generate a partially corrected joint angle of the hip joint, if the inclination of the trunk is greater than a threshold value; and
    correcting the partially corrected joint angle of the hip joint based on the movement of the pelvis, if a range of a movement of the hip joint is less than a threshold range.

10. The method of claim 1, wherein the controlling comprises:
    detecting a gait cycle of the user based on the corrected movement information of the hip joint; and
    determining the torque to apply to the walking assistance apparatus based on the gait cycle.

11. The method of claim 10, wherein
    the detecting includes detecting a phase of a gait cycle of a first leg of the user based on the corrected movement information of the hip joint, and
    the determining includes determining a torque corresponding to the phase of the gait cycle.

12. The method of claim 1, wherein the measuring comprises:
    measuring a movement of a hip joint of a first leg of a pair of legs of the user, the first leg being a leg that does not function normally.

13. A walking assistance apparatus comprising:
    a sensor configured to measure a movement of a hip joint of a user associated with the walking assistance apparatus and a movement of another portion of a body of the user;
    a driver configured to assist the user in walking; and
    a processor configured to,
        correct movement information of the hip joint based on movement information of the other portion of the body to generate corrected movement information, and
        control a torque to apply to the driver based on the corrected movement information of the hip joint.

14. The apparatus of claim 13, wherein
    the sensor includes a first sensor configured to measure the movement of the hip joint and a second sensor configured to measure a movement of a pelvis of the user, and
    the processor is configured to correct a joint angle associated with the movement of the hip joint based on the movement of the pelvis.

15. The apparatus of claim 13, wherein
    the sensor includes a first sensor configured to measure the movement of the hip joint and a second sensor configured to measure an inclination of a trunk of the user, and
    the processor is configured to correct a joint angle associated with the movement of the hip joint based on the inclination of the trunk.

16. The apparatus of claim 13, wherein
    the sensor includes a first sensor configured to measure the movement of the hip joint, a second sensor configured to measure a movement of a pelvis of the user, and a third sensor configured to measure an inclination of a trunk of the user, and
    the processor is configured to correct a joint angle associated with the movement of the hip joint based on the movement of the pelvis and the inclination of the trunk.

17. The apparatus of claim 16, wherein
    the first sensor includes at least one of a potentiometer, an absolute encoder, and an incremental encoder, and
    the second sensor and the third sensor each include at least one of an acceleration sensor, an inclination sensor, an inertial sensor, and a gyrosensor.

18. A method of controlling a walking assistance apparatus, the method comprising:

determining, via a processor, a gait cycle of a user based on a corrected joint angle of a hip joint of the user, the gait cycle of the user being abnormal; and
instructing, via the processor, a driver of the walking assistance apparatus to drive the walking assistance apparatus at a torque level determined based on the gait cycle, wherein
  a joint angle of the hip joint of the user is measured by a sensor of the walking assistance apparatus and is corrected so that the corrected joint angle is obtained, and
  the driver is configured to assist the user in walking.

19. The method of claim 18, further comprising:
determining, by the processor, a phase of the gait cycle based on at least one of a particularly-shaped adaptive oscillator (PSAO), an adaptive frequency oscillator (AFO), and a finite state machine (FSM); and
determining, by the processor, the torque level from torque data based on the gait cycle.

20. The method of claim 19, wherein the torque data defines a corresponding relationship between the phase of the gait cycle and the torque level.

21. The method of claim 18, further comprising:
measuring, via one or more sensors, a measured joint angle of the hip joint of the user;
measuring, via the one or more sensors, one or more of an inclination of a trunk of the user and a rotational angular velocity of a pelvis of the user; and
selectively correcting, by the processor, the measured joint angle based on whether one or more of the inclination of the trunk and the rotational angular velocity of the pelvis is outside a threshold range.

22. The method of claim 21, wherein the selectively correcting comprises:
determining, by the processor, the corrected joint angle based on the measured joint angle of the hip joint and one or more of the inclination of the trunk and the rotational angular velocity of the pelvis.

23. The method of claim 21, wherein the determining the corrected joint angle comprises:
removing, by the processor, an angle of forward inclination of the trunk of the user from the measured joint angle.

* * * * *